United States Patent [19]
Troffer et al.

[11] Patent Number: 5,872,318
[45] Date of Patent: Feb. 16, 1999

[54] METHOD AND APPARATUS FOR INDUCING FULLY-REVERSED THREE-DIMENSIONAL LOADING ON A NON-ROTATING BEAM

[75] Inventors: Michael A. Troffer, Waldorf; William Minor Appleman, Davidsonville; Joseph F. Korczynski, Jr., Glen Burnie, all of Md.

[73] Assignee: The United States of America as represented by the Secretary of the Navy, Washington, D.C.

[21] Appl. No.: 819,561

[22] Filed: Mar. 14, 1997

[51] Int. Cl.$^6$ .................................................... G01N 3/20
[52] U.S. Cl. ................................... 73/849; 73/854
[58] Field of Search ........................... 73/843, 847, 849, 73/852, 854

[56] References Cited

U.S. PATENT DOCUMENTS

| | | | |
|---|---|---|---|
| 1,760,033 | 5/1930 | Amsler . | |
| 3,112,643 | 12/1963 | Lanahan | 73/162 |
| 3,672,212 | 6/1972 | Caspary et al. | 73/99 |
| 3,797,304 | 3/1974 | Klinger | 73/849 |
| 4,517,843 | 5/1985 | Leger | 73/847 |
| 5,501,110 | 3/1996 | Peilloud et al. | 73/862.321 |
| 5,591,921 | 1/1997 | Schaede | 73/849 |

*Primary Examiner*—George M. Dombroski
*Assistant Examiner*—Max H. Noori
*Attorney, Agent, or Firm*—Howard Kaiser

[57] ABSTRACT

The inventive fatigue-testing apparatus features a compact orbital mechanism which rotates a bending force around a non-rotating test section and a stationary test bed. In addition to applying a bending force, some inventive embodiments apply an axial force and a torsional force, thereby accomplishing full-scale evaluation of test sections under three-dimensional loading; the inventive practice for applying bending, torsional and axial loads compares favorably with conventional practice in terms of reliability and cost. The inventive orbital mechanism increases the reliability of the entire inventive test apparatus by reducing the number of moving parts, component wear, maintenance and complexity. The invention also provides maximum access to the test section for instrumentation, inspection, maintenance and modification. The inventive benefits will permit evaluations of larger test sections and will afford extended evaluations to more accurately determine fatigue limitations of complex joints.

20 Claims, 7 Drawing Sheets

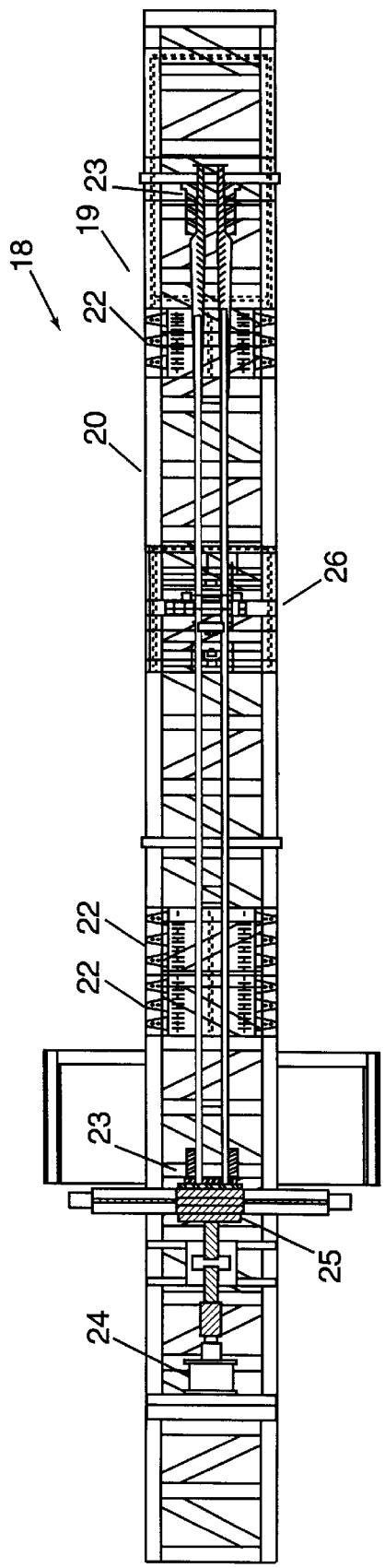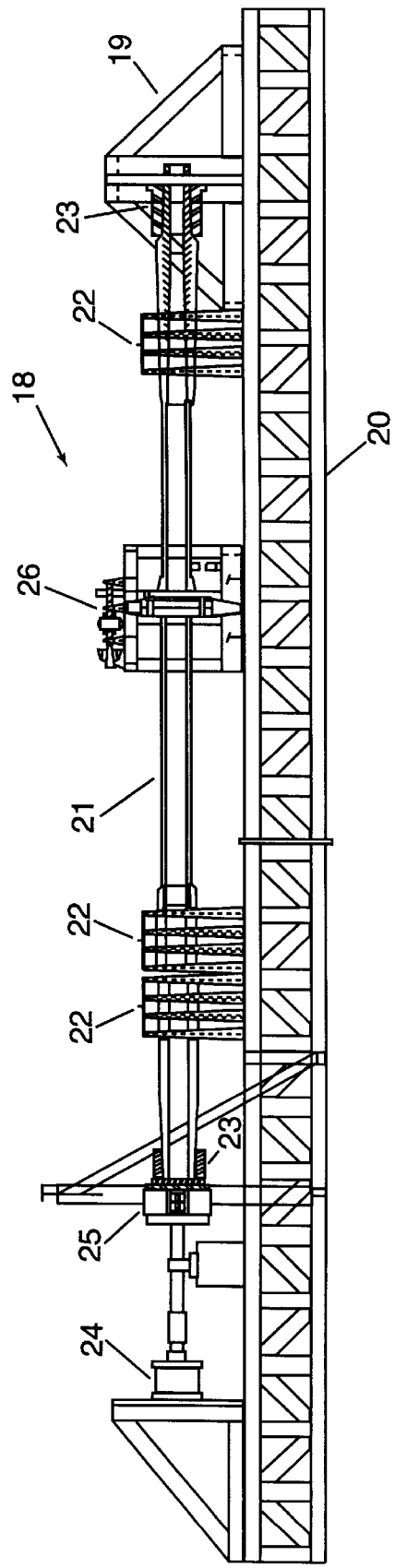
FIG. 1
FIG. 2

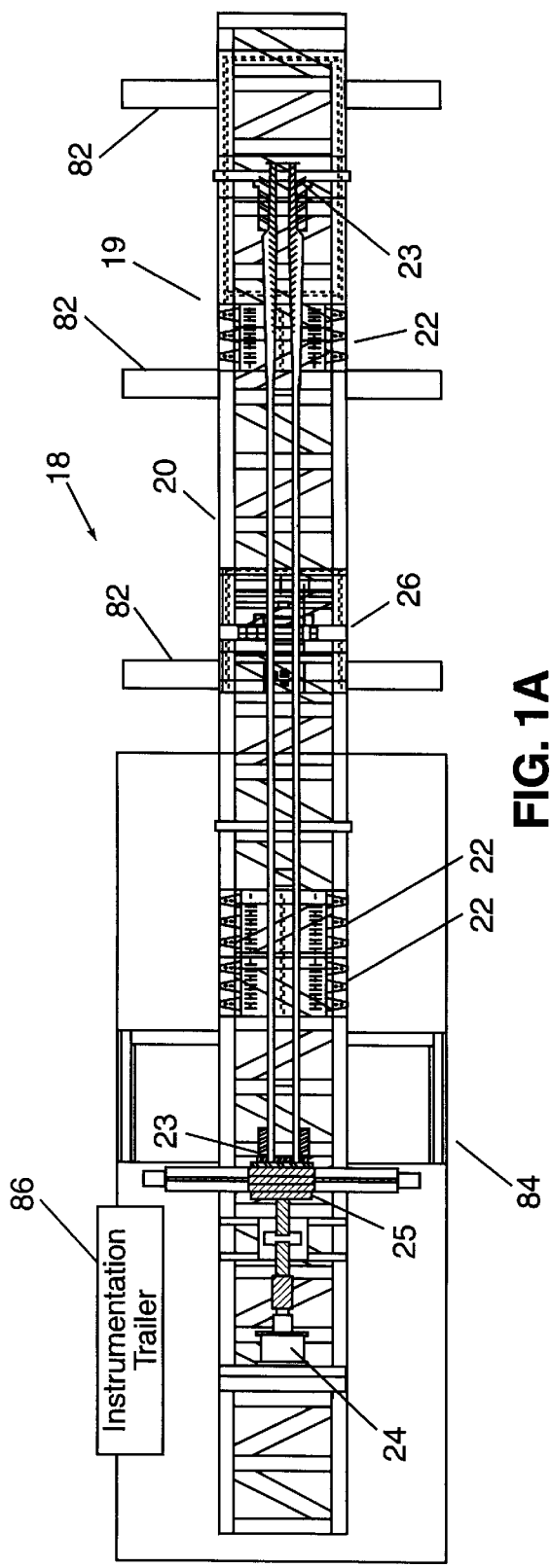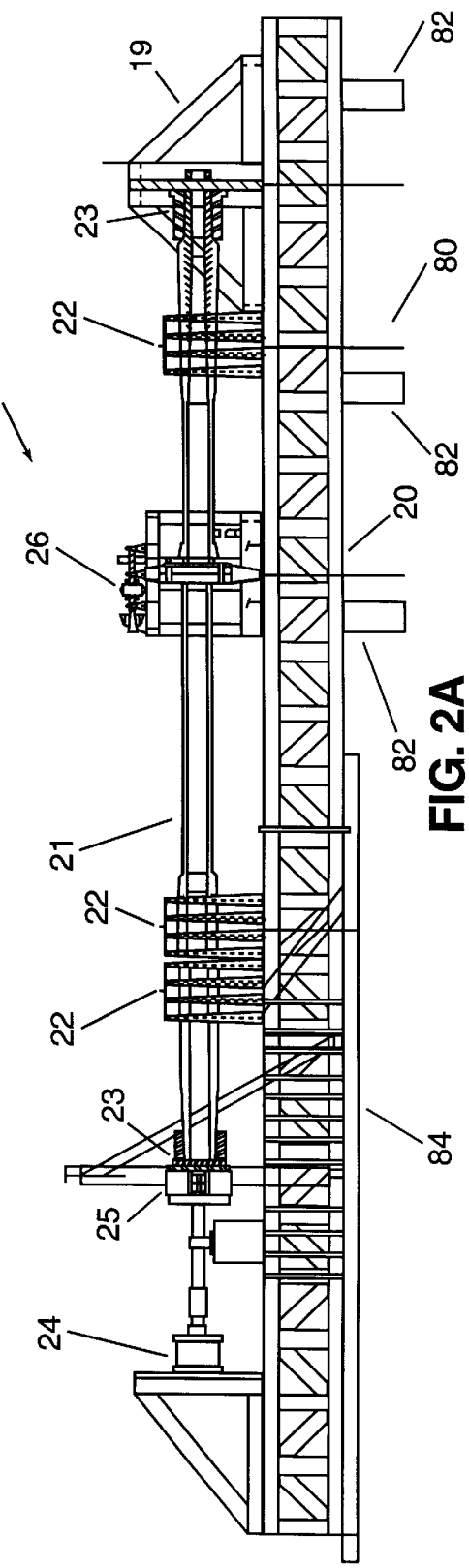
FIG. 1A
FIG. 2A

METHOD AND APPARATUS FOR INDUCING FULLY-REVERSED THREE-DIMENSIONAL LOADING ON A NON-ROTATING BEAM

The invention described herein may be manufactured and used by or for the Government of the United States of America for governmental purposes without the payment of any royalties thereon or therefor.

BACKGROUND OF THE INVENTION

The present invention relates to methods and apparatuses for testing structural properties of structural members, more particularly to methods and apparatuses for testing fatigue of structural members having complex joints.

For certain kinds of structural members, conventional approaches to evaluating fatigue have not been entirely satisfactory. In particular, there remains a need for a practical yet accurate fatigue testing methodology for shaft-like structural members containing complex joints at both ends, especially for such members which are made of heterogeneous materials. Generally speaking, systems of complex joints which utilize a variety of materials have unpredictable fatigue characteristics.

The U.S. Navy has conducted cyclic fatigue testing of structural members comprising fiber-reinforced polymer-matrix composite and titanium materials. In order to reduce costs, such testing by the Navy has typically been relegated to small-scale model testing or coupon testing. However, the Navy has had limited success in extrapolating these test results so as to accurately predict full-scale long term fatigue strength for joints which utilize fiber-reinforced polymer-matrix composite and titanium materials in a propulsion shafting system.

SUMMARY OF THE INVENTION

In view of the foregoing, it is an object of the present invention to provide accurate, efficient and economical apparatus and method for conducting full-scale, long-term cyclic fatigue evaluations on a shafting system.

It is a further object of this invention to provide such apparatus and method for conducting such evaluations on a shafting system which is non-homogenous and/or complexly jointed.

Another object of this invention is to provide such apparatus and method which optimally affords access to the test section for purposes of instrumentation, inspection, maintenance and modification.

The present invention uniquely features a compact orbital mechanism which rotates a bending force generated by a radial load which is induced by a radial displacement/offset around a fixed full-scale test section. The inventive orbital mechanism permits non-rotation of the test section during fully-reversed loading.

In accordance with this invention, an orbital device is used for rotatively selectively applying a bending moment to a non-rotating object. The orbital device comprises a primary annulus and a secondary annulus. The primary annulus is capable of primary rotation about an imaginary primary axis. The secondary annulus is capable of substantially nonfrictional secondary rotation about an imaginary secondary axis during the primary rotation. The imaginary primary axis and the imaginary secondary axis are approximately parallel. The primary annulus approximately defines an imaginary primary cylinder with respect to the imaginary primary axis. The secondary annulus approximately defines an imaginary secondary cylinder with respect to the imaginary secondary axis. The imaginary primary cylinder approximately encompasses the imaginary secondary cylinder. A bending moment is capable of being applied to an object passing through the secondary annulus so that the bending moment changes during the primary rotation in accordance with the orbit of the imaginary secondary axis about the imaginary primary axis.

Hence, according to this invention, the primary annulus is larger than the secondary annulus, and the primary and secondary axes are noncoincident. According to many inventive embodiments, the secondary annulus is disposed, eccentrically and approximately coplanarly, inside the primary annulus.

Many preferred inventive embodiments provide an orbital device which comprises an inner rolling element bearing assembly, an outer rolling element bearing assembly and an intermediate structure. The inner rolling element bearing assembly inwardly includes the secondary annulus. The outer rolling element bearing assembly inwardly includes the primary annulus. The intermediate structure unites the inner rolling element bearing assembly and the outer rolling element bearing assembly.

This invention minimizes the number of moving elements, permits greater accessibility to the test section, and eliminates the need to rotate the test section, thereby improving the reliability and affordability of the evaluation. The invention provides maximum access to the test section for instrumentation, inspection, maintenance and modification. The inventive orbital mechanism reduces component wear, the number of moving parts, maintenance and complexity, resulting in a more reliable system. Overall, these inventive benefits will permit testing of larger test sections and afford extended testing to more accurately determine fatigue limits.

The inventive orbital device offers design simplicity and the ability to operate unattended for long periods of time; hence, the invention is well suited for fully reversing fatigue loading requiring long term cycling. The present invention is particularly important for testing complex joints which utilize a variety of materials which, as a system, have unpredictable fatigue characteristics.

The U.S. Navy has developed and demonstrated an inventive embodiment for use in testing lightweight fiber-reinforced polymer-matrix composite and titanium shafting joints for marine vehicles, a use for which long-term cyclic fatigue strength is a critical safety issue. Many inventive embodiments, such as the U.S. Navy's inventive prototype, test the structural integrity of cylindrically or non-cylindrically shaped beams and joints under fully reversing bending, torsional and axial loads.

According to such embodiments of this invention, a non-rotating test section has rigidly fixed end connections through which torsional and axial loads can be independently applied. In the vicinity of the axially longitudinal middle of the test section, the inventive orbital mechanism articulates fully reversing bending by rotating a radial displacement/offset 360 degrees in an orbiting motion around the test section. The bending, torsional and axial loads can be applied independently at different frequencies and magnitudes to simulate a wide range of physical forces experienced in complex structures. The inventive orbital mechanism is the unique device which allows non-rotation of the test section during fully-reversed loading.

Other objects, advantages and features of this invention will become apparent from the following detailed description of the invention when considered in conjunction with the accompanying drawings.

BRIEF DESCRIPTION OF THE DRAWINGS

In order that the present invention may be clearly understood, it will now be described, by way of example, with reference to the accompanying drawing, wherein like numbers indicate the same or similar components, and wherein:

FIG. 1 is a diagrammatic top plan view of an embodiment of test apparatus in accordance with the present invention, including the inventive orbital mechanism.

FIG. 1A is a diagrammatic view, similar to the view shown in FIG. 1, of the inventive embodiment shown in FIG. 1, additionally showing some base structure.

FIG. 2 is a diagrammatic side elevation view of the inventive embodiment shown in FIG. 1.

FIG. 2A is a diagrammatic view, similar to the view shown in FIG. 2, of the inventive embodiment shown in FIG. 1, additionally showing some base structure.

DETAILED DESCRIPTION OF THE INVENTION

Figure 3:
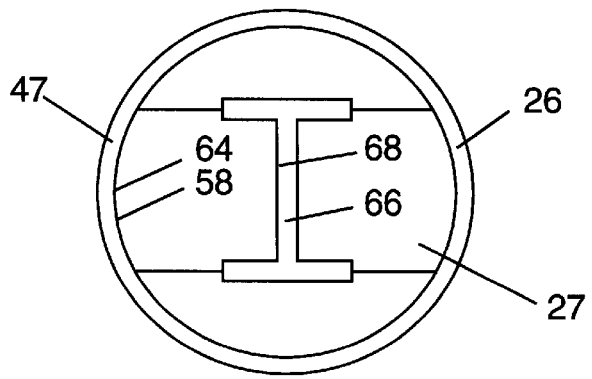
FIG. 3 is a diagrammatic partial elevation view of a four-piece mandrel used to interface an I-beam test section and the inner bearing housing of the inventive orbital mechanism.

Referring now to FIG. 1 and FIG. 2, inventive apparatus 18 includes stationary test bed 19, which is utilized to provide a rigid foundation upon which to measure test section deflections and stresses. Stationary test bed 19 includes support beams and bearings and underframe 20. I-beams and conventional construction techniques are used to minimize cost.

Cylindrical test section 21 is rigidly supported by three sets of clamp bearings 22 and two fixed end connections 23. Axial and torsional forces are applied with hydraulic actuators 24 and 25, respectively.

Clamp bearings 22 establish the "boundary conditions" for the bending moment testing. The bending moment profile is essentially defined in terms of the position of orbital mechanism 26 and the positions of clamp bearings 22; i.e., the operator of the inventive apparatus selects values for various parameters, including the distance of clamp bearings 22 from each other, the respective distances of clamp bearings 22 from orbital mechanism 26, and the respective distances of clamp bearings 22 from the longitudinal ends of cylindrical test section 21.

Orbital mechanism 26 is used to provide a fully-reversing bending moment on non-rotating test section 21. This is achieved by rotating a radial displacement/offset 360 degrees around test section 21, thereby creating an orbital motion; the rotational speed of this radial displacement/ offset-induced load will determine the frequency of the bending moment.

Referring to FIG. 1A and FIG. 2A, inventive apparatus 18 sits on an underlying foundation such as concrete base 80, which includes supports 82 and pad 84. Apparatus 18 is not fixed with respect to base 80 but, rather, merely rests on base 80. The loads are reacted by apparatus 18 only. Instrumentation trailer 86 is conveniently located.

With reference to FIG. 3, the inventive apparatus can also accommodate test sections with non-circular cross-sections. One or more mandrels or spindles such as mandrel 27 can be used for interfacing with circular supports such as clamp bearings 22, end connections 23 and orbital mechanism 26. Mandrel 27 exemplifies a mandrel or spindle which can be used for a conventional I-beam.

Figure 4:
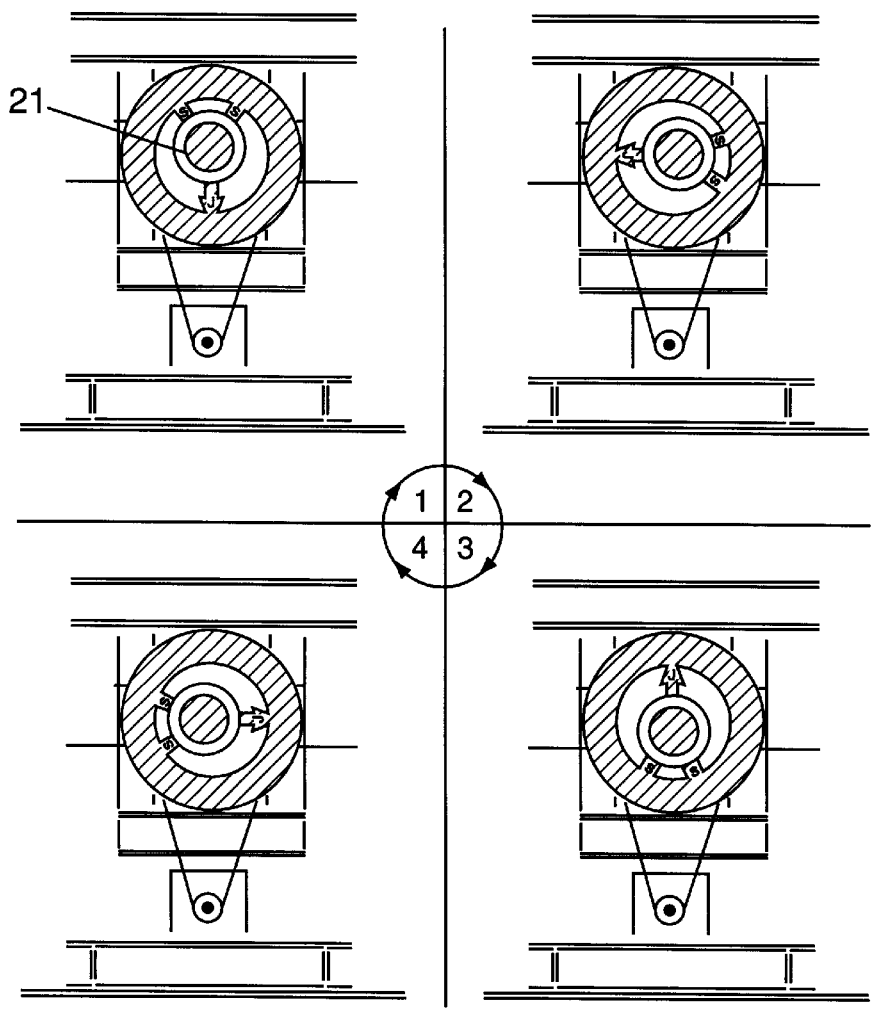
FIG. 4 is a diagrammatic illustration of the test section's orbital motion produced by the inventive orbital mechanism's wedge/shim system.

Reference now being made to FIG. 4, the radial displacement/offset-induced load is applied to test section 21 by a system of wedges and shims which displaces test section 21 from its longitudinal center line. The radial displacement/offset-induced load is rotated through four quadrants (first, second, third and fourth quadrants, indicated by "1," "2," "3" and "4," respectively) around test section 21.

Test section 21 is bent so as to be displaced from its longitudinal axis of centricity, i.e., the imaginary line which would define the longitudinal center of test section 21 if test section 21 remained unbent. The displacement of test section 21 from its center line is adjusted for the desired reaction moments at the "fixed-fixed" end connections 23. This displacement is a function of the radial load, the rigidity and positions of end connections 23, and the flexural rigidity of test section 21.

Figure 5:
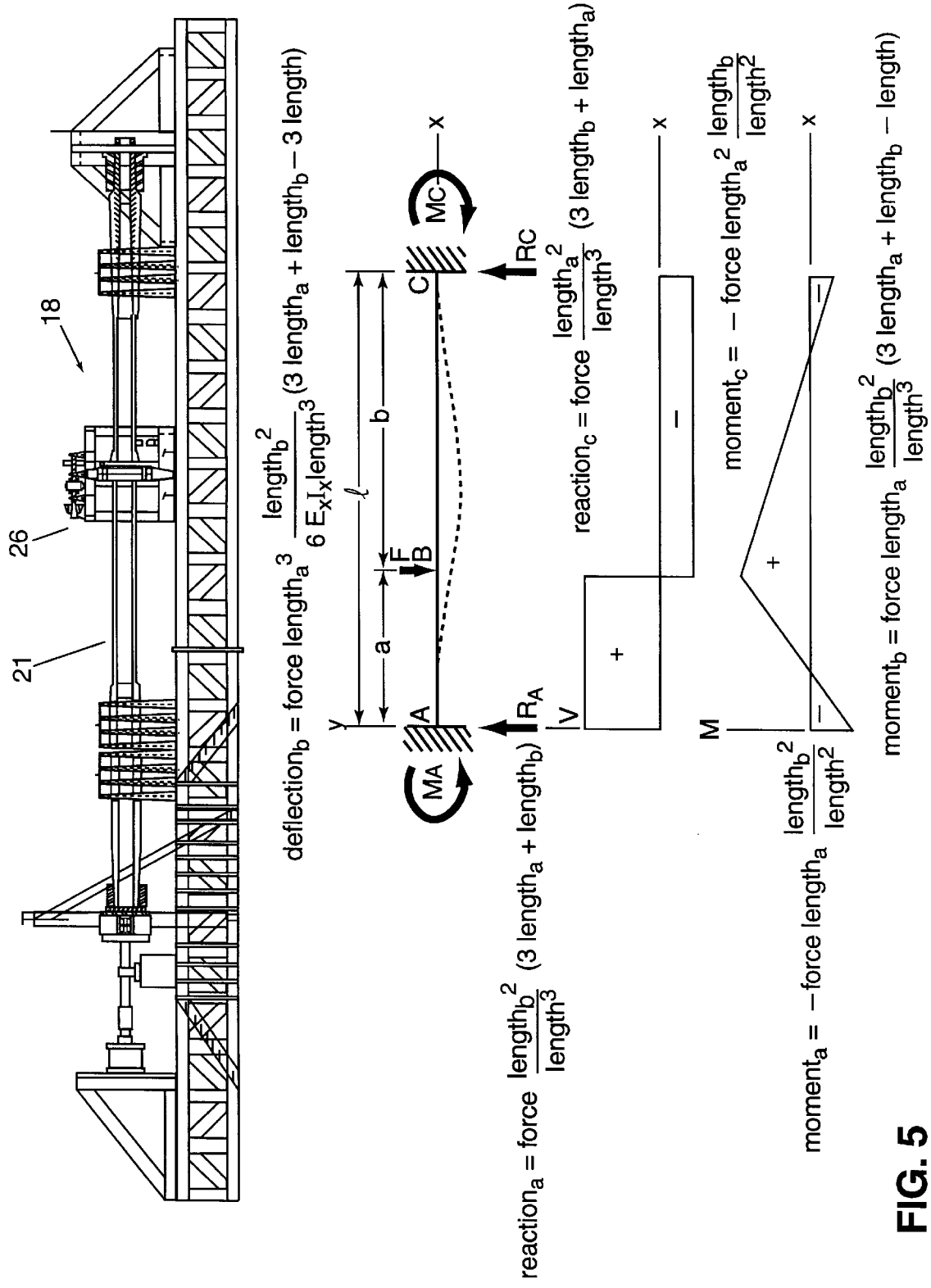
FIG. 5 is a diagrammatic view, similar to the view shown in FIG. 2, of the inventive embodiment shown in FIG. 1, additionally illustrating the corresponding bending produced by the inventive orbital mechanism.

Referring to FIG. 5, shown are the beam shear and bending moment equations which govern the relationship between the force applied by orbital mechanism 26 and the resultant bending moments induced on test section 21.

Rolling element bearings (also commonly referred to as "roller" bearings or "rolling-contact" bearings) are conventionally used for locating and supporting machine parts such as rotors or rotating shafts. Typically, the rolling elements of a roller bearing are balls or rollers. In general, a roller bearing is a type of anti-friction bearing; a roller bearing serves to minimize friction so as to permit relatively free rotation. A conventional roller bearing essentially consists of a plurality of rolling elements in rolling contact with the corresponding inside raceway surfaces of an inner bearing ring and an outer bearing ring.

Figure 6:
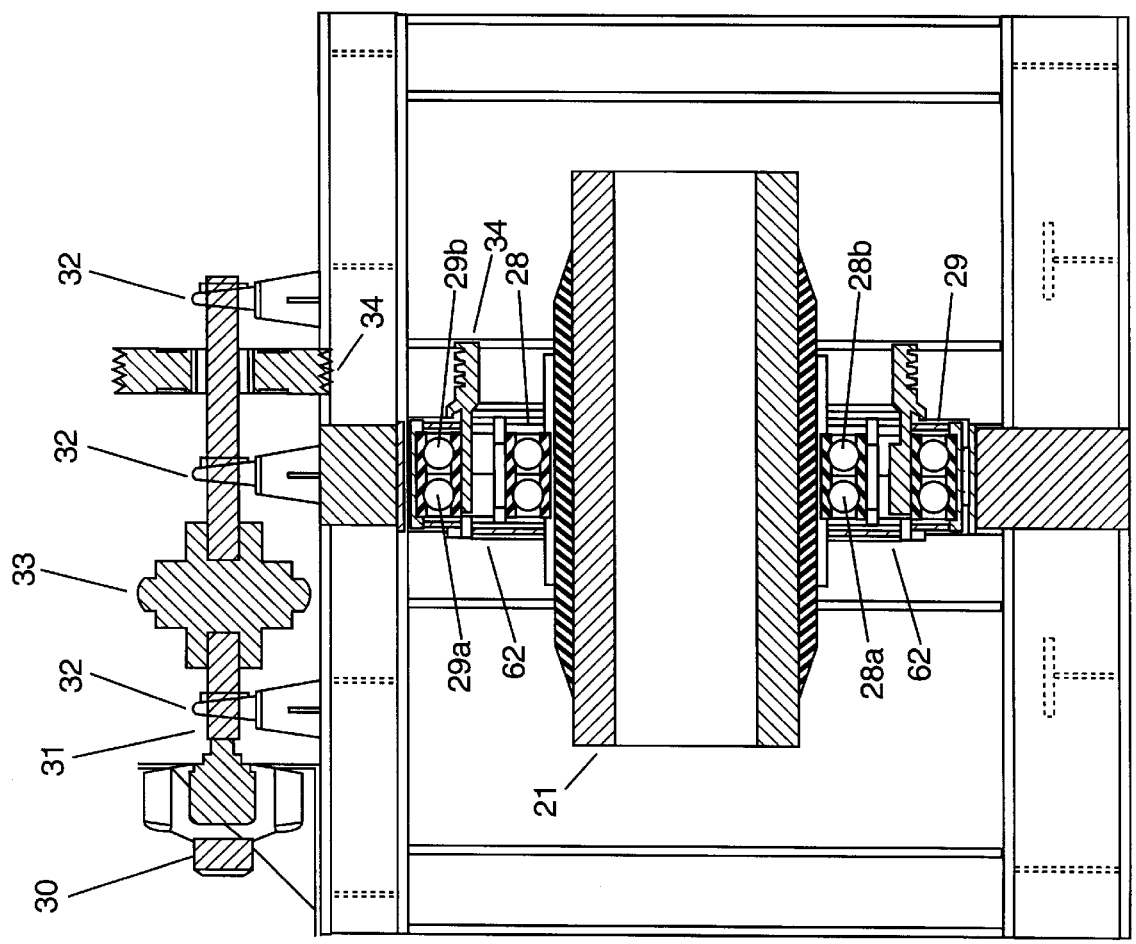
FIG. 6 is a diagrammatic partial cross-sectional view of the inventive orbital mechanism.

With reference to FIG. 6, a dual set of rolling element bearings is inventively implemented to afford the off-center orbital displacement of test section 21. Radially inner roller bearing assembly 28 and radially outer roller bearing assembly 29 are configured to together provide a compact, low-friction interface between non-rotating test section 21 and stationary test bed 19.

Radially inner roller bearing assembly 28 as shown includes two adjacent equally sized roller bearings, viz., radially inner roller bearing 28a and radially inner roller bearing 28b. Radially outer roller bearing assembly 29 as shown also includes two adjacent equally sized roller bearings, viz., radially outer roller bearing 29a and radially outer roller bearing 29b. Outer roller bearings 29a and 29b are larger than inner roller bearings 28a and 28b.

Inner roller bearing 28a has inner bearing inner ring 50a, inner bearing outer ring 51a and inner bearing rolling elements 52a. Inner roller bearing 28b has inner bearing inner ring 50b, inner bearing outer ring 51b and inner bearing rolling elements 52b. Accordingly, inner roller bearing assembly 28 has inner bearing assembly inner ring 50 (which includes inner bearing inner rings 50a and 50b), inner bearing assembly outer ring 51 (which includes inner bearing outer rings 51a and 51b) and inner bearing rolling elements 52 (which include inner bearing rolling elements 52a and 52b).

Similarly, outer roller bearing 29a has outer bearing inner ring 53a, outer bearing outer ring 54a and outer bearing rolling elements 55a. Outer roller bearing 29b has outer bearing inner ring 53b, outer bearing outer ring 54b and outer bearing rolling elements 55b. Accordingly, outer roller bearing assembly 29 has outer bearing assembly inner ring 53 (which includes outer bearing inner rings 53a and 53b), outer bearing assembly outer ring 54 (which includes outer bearing outer rings 54a and 54b) and outer bearing rolling elements 55 (which include inner bearing rolling elements 55a and 55b).

Roller bearing assemblies 28 and 29 each have two parallel raceways. In this example, roller bearing assemblies 28 and 29 each comprise a combination of two abutting single-row roller bearings, each of which has been manufactured as a unit. As an alternative inventive approach to providing two rows of rolling elements for each roller bearing assembly, roller bearing assemblies 28 and 29 can each comprise a single double-row roller bearing which has been manufactured as a unit. In inventive practice, the selection of roller bearing assemblies 28 and 29, e.g., in terms of size and number of rows, depends on the application requirements, e.g., in terms of the test section and the radially loading characteristics.

Power is derived from a transmission system which is driven by hydraulic motor 30. The transmission system comprises standard shaft 31, bearings 32, flexible coupling 33 and V-belt drive 34.

Figure 7:
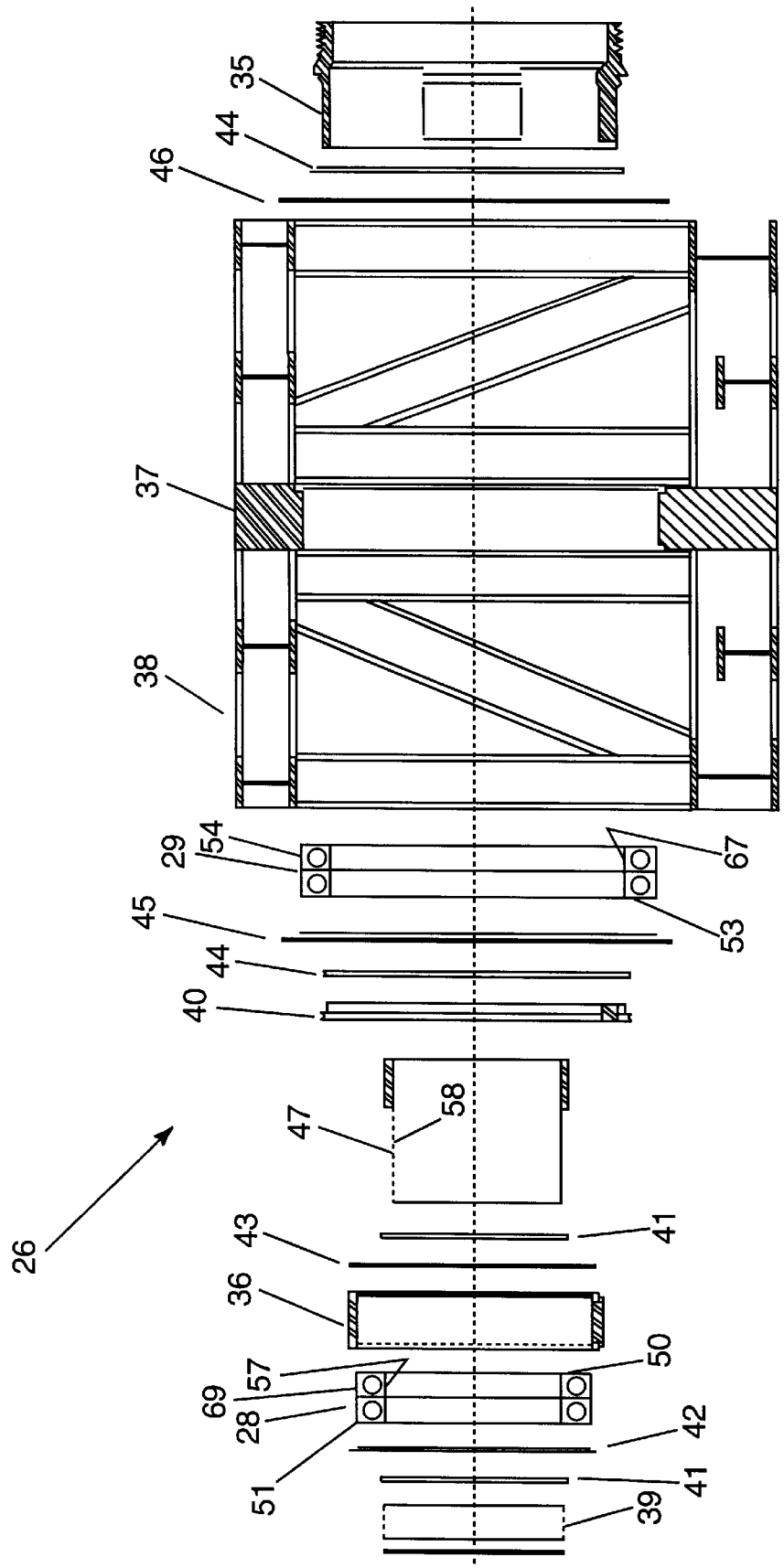
FIG. 7 is a diagrammatic exploded cross-sectional view of the orbital mechanism, showing the alignment of major components.
Figure 8:
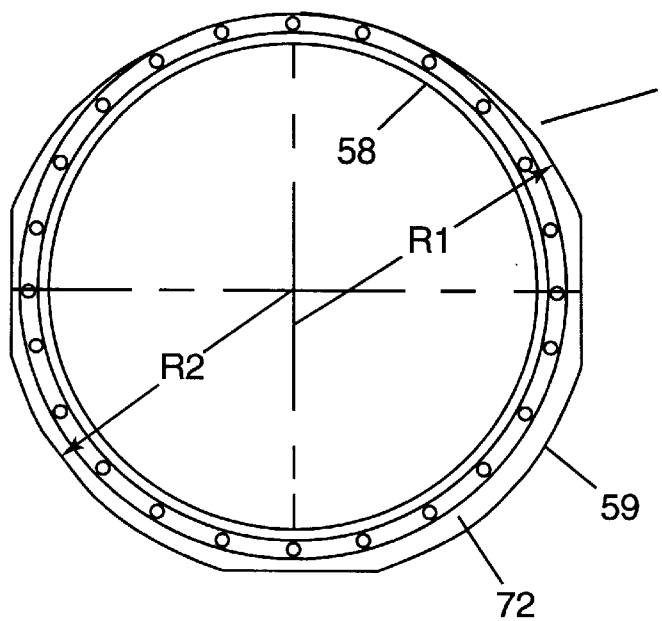
FIG. 8 is a diagrammatic elevation view of the outer shell which fits on the inner bearing's outer ring.
Figure 9:
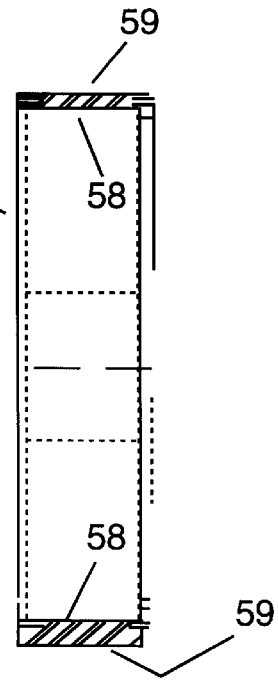
FIG. 9 is a diagrammatic cross-sectional view of the outer shell shown in FIG. 8.
Figure 10:
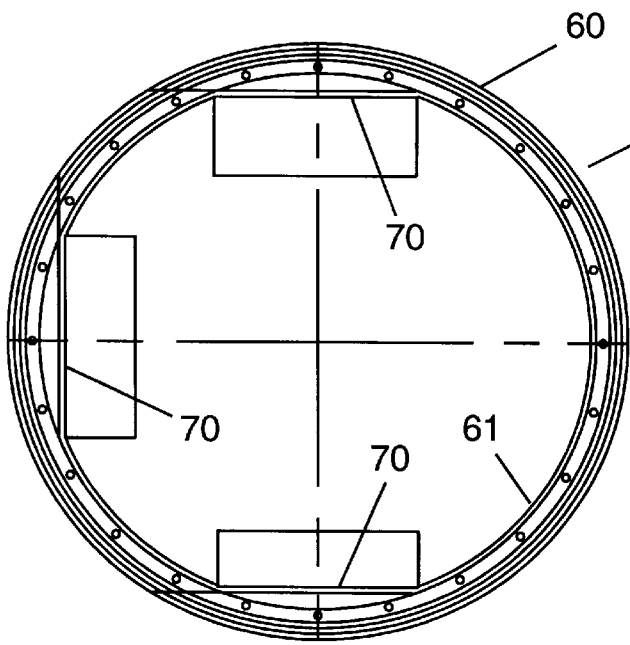
FIG. 10 is a diagrammatic elevation view of the inner shell which fits on the outer bearing's inner ring.
Figure 11:
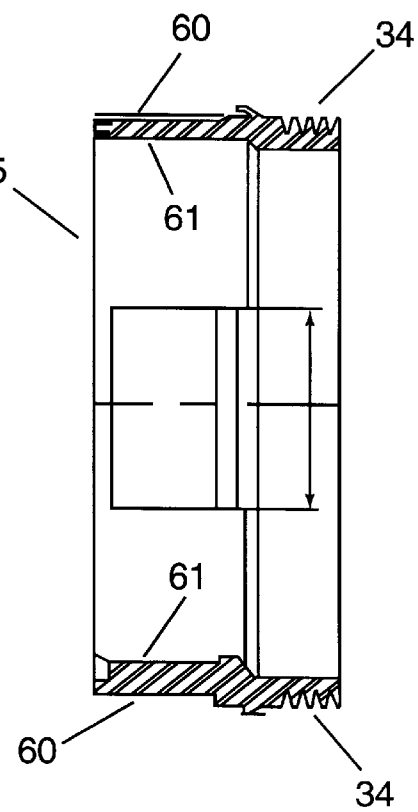
FIG. 11 is a diagrammatic cross-sectional view of the inner shell shown in FIG. 10.

Referring to FIG. 7, the basic internal assembly of orbital mechanism 26 is shown along with the working relationship among some components. To insure rigid alignment in inventive testing apparatus 18, outer housing 37 of outer roller bearing assembly 29 is affixed to outer bearing assembly outer ring 54 and secured to a network of support beams 38, which are attached to underframe 20 shown in FIG. 2. To minimize contamination, leakage and wear, the bearings are protected by a system of retainer rings 39 and 40 and seals 41, 42, 43, 44, 45 and 46.

Still referring to FIG. 6 and FIG. 7, and also referring to FIG. 8 through FIG. 11, inner roller bearing assembly 28 is provided with shells 47 and 36, and outer roller bearing assembly 29 is provided with shell 35. Each shell is a cartridge-type or modular-type unit which fits, bushing-like, inside or outside the circumferential (annular peripheral) surface of a roller bearing ring.

In accordance with many embodiments of this invention, an adaptor is coupled with the annular inner peripheral (bore) surface 57 of inner bearing assembly inner ring 50, for purposes of accommodating test sections 21 having any of various cross-sectional shapes. For accommodating cross-sectionally circular test sections 21, the adaptor comprises circular (ring-shaped) inner bearing assembly inner shell 47. For accommodating cross-sectionally non-circular test sections 21, the adaptor comprises the combination of inner bearing assembly inner shell 47 and mandrel 27.

Inner roller bearing assembly 28 is radially inwardly provided with inner bearing assembly inner shell 47. Inner bearing assembly inner shell 47 has annular peripheral surfaces both inside and outside. The annular outer peripheral surface 56 of inner bearing assembly inner shell 47 is in conformity with the annular inner peripheral (bore) surface 57 of inner bearing assembly inner ring 50, thereby permitting joinder of inner roller bearing assembly 28 and inner bearing assembly inner shell 47.

Inner bearing assembly inner shell 47 has an annular inner peripheral surface 58 which can accomodate test sections 21 which are circular in cross-section. Alternatively, a mandrel or spindle, such as mandrel 27 shown in FIG. 3, is incorporated inside inner bearing assembly inner shell 47. Referring again to FIG. 3, mandrel 27 has an annular outer peripheral mandrel surface 64 which is in conformity with annular inner peripheral surface 58 of inner bearing assembly inner shell 47. Mandrel 27 has a mandrel aperture 66 defining an inner peripheral aperture surface 68 which can accomodate test sections 21 which are non-circular in cross-section.

Still referring to FIG. 6 through FIG. 11, inner roller bearing assembly 28 is radially outwardly provided with inner bearing assembly outer shell 36. Outer roller bearing assembly 29 is radially inwardly provided with outer bearing assembly inner shell 35. Inner bearing assembly outer shell 36 has an annular inner peripheral surface 58 and a non-annular outer peripheral surface 59. Outer bearing assembly inner shell 35 has an annular outer peripheral surface 60 and a non-annular inner peripheral surface 61.

The annular outer peripheral surface 60 of outer bearing assembly inner shell 35 is in conformity with the annular inner peripheral surface 67 of outer bearing assembly inner ring 53, thereby permitting joinder of outer roller bearing assembly 29 and outer bearing assembly inner shell 35. The annular inner peripheral surface 58 of inner bearing assembly outer shell 36 is in conformity with the annular outer peripheral surface 69 of inner bearing assembly outer ring 51, thereby permitting joinder of inner roller bearing assembly 28 and inner bearing assembly outer shell 36.

The non-annular outer peripheral surface 59 of inner bearing assembly outer shell 36 and the non-annular inner peripheral surface 61 of outer bearing assembly inner shell 35 each have a complementary irregular shape; these complementary irregular peripheral surfaces mate inner bearing assembly outer shell 36 and outer bearing assembly inner shell 35.

Together, inner bearing assembly outer shell 36 and outer bearing assembly inner shell 35 form an eccentrically apertured orbital displacement system 62 which, radially interpositionally between the radially inner ring 53 of outer roller bearing assembly 29 and the radially outer ring 51 of inner roller bearing assembly 28, provides eccentricity of the inner ring 50 of inner roller bearing assembly 28 (and hence of inner bearing inner shell 47) with respect to the rotational axis of the inner ring 53 of outer roller bearing assembly 29. This eccentricity enables the orbital displacement of test section 21, which passes through, and is held by, inner bearing assembly inner shell 47.

FIG. 8 through FIG. 11 show details of a "wedge/shim" system in accordance with the present invention. The non-annular inner peripheral surface 61 of outer bearing assembly inner shell 35 is irregularly configured so to have three wedge-like areas 70 which are circumferentially disposed approximately ninety degrees apart. The non-annular outer peripheral surface 59 of inner bearing assembly outer shell 36 is irregularly configured so to have a shim-like area 72 which extends less than 360° circumferentially and which serves to centrically skew the annular inner peripheral surface 58 of inner bearing assembly outer shell 36.

Outer bearing assembly inner shell 35 interlocks with inner bearing assembly outer shell 36; this combination provides a wedge/shim system which produces the orbital displacement of test section 21. While outer bearing assembly inner ring 53 is caused to rotate, test section 21 freely (substantially frictionlessly) rotates about the central rotational axis of inner bearing assembly inner ring 50 and eccentrically revolves around ("orbits") the central rotational axis of outer bearing assembly inner ring 53.

The magnitude of the resulting bending force can be adjusted by varying one or more dimensional parameters, viz., the radial dimensions of orbital displacement system 62 and the wedge/shim "off-set" dimensions. The radial dimensions of orbital displacement system 62 can be selected by varying the radial dimensions of inner bearing outer shell 36 and/or the radial dimensions of outer bearing inner shell 35.

Other embodiments of this invention will be apparent to those skilled in the art from a consideration of this specification or practice of the invention disclosed herein. Various omissions, modifications and changes to the principles described may be made by one skilled in the art without departing from the true scope and spirit of the invention which is indicated by the following claims.

What is claimed is:

1. An orbital device for rotatively selectively applying a bending moment to a non-rotating object, said orbital device comprising a primary annulus and a secondary annulus, said primary annulus being capable of primary rotation about an imaginary primary axis, said secondary annulus being capable of substantially nonfrictional secondary rotation about an imaginary secondary axis during said primary rotation, said imaginary primary axis and said imaginary secondary axis being approximately parallel, said primary annulus approximately defining an imaginary primary cylinder with respect to said imaginary primary axis, said secondary annulus approximately defining an imaginary secondary cylinder with respect to said imaginary secondary axis, said imaginary primary cylinder approximately encompassing said imaginary secondary cylinder, wherein said bending moment is capable of being applied to a said object passing through said secondary annulus so that said bending moment changes during said primary rotation in accordance with the orbit of said imaginary secondary axis about said imaginary primary axis.

2. An orbital device as in claim 1, wherein said secondary annulus is eccentrically and approximately coplanarly disposed inside said primary annulus.

3. An orbital device as in claim 1, wherein said orbital device comprises:
 a primary rolling element bearing assembly which includes said primary annulus, a primary opposite annulus and an interposed plurality of primary rolling elements, said primary annulus being radially interiorly situated in said primary rolling element bearing assembly, said primary opposite annulus being radially exteriorly situated in said primary rolling element bearing assembly;
 a secondary rolling element bearing assembly which includes said secondary annulus, a secondary opposite annulus and an interposed plurality of secondary rolling elements, said secondary annulus being radially interiorly situated in said secondary rolling element bearing assembly, said secondary opposite annulus being radially exteriorly situated in said secondary rolling element bearing assembly; and
 means for connecting said primary annulus and said secondary opposite annulus.

4. An orbital device as in claim 3, wherein said means for connecting includes:
 a primary shell which is radially interiorly coupled with said primary annulus, said primary shell having a shape which is radially exteriorly circular and which is radially interiorly noncircular; and
 a secondary shell which is radially exteriorly coupled with said secondary opposite annulus and which is radially interiorly coupled with said primary shell, said secondary shell having a shape which is radially exteriorly noncircular and which is radially interiorly circular.

5. An orbital device as in claim 4, wherein said orbital device comprises a tertiary shell which is radially interiorly coupled with said secondary ring, said tertiary shell having a shape which is radially exteriorly circular and which is radially interiorly circular.

6. An orbital device as in claim 5, wherein said object has a shape which is circular in cross-section and which fits inside said tertiary shell.

7. An orbital device as in claim 5, wherein said orbital device comprises a mandrel having a shape which is radially exteriorly circular and which fits inside said tertiary shell, said mandrel including a mandrel opening having a shape which is radially interiorly non-circular, said object having a shape which is non-circular in cross-section and which fits inside said mandrel opening.

8. An orbital device as in claim 1, wherein said orbital device comprises:
 a first rolling element bearing assembly, said first rolling element bearing assembly including a first radially inner ring and a first radially outer ring, said first radially inner ring having a first nonracewayed radially inner peripheral surface, said first radially outer ring having a first nonracewayed radially outer peripheral surface;
 a second rolling element bearing assembly which is situated eccentrically substantially coplanarly inward of said first rolling element bearing assembly, said second rolling element bearing assembly including a second radially inner ring and a second radially outer ring, said second radially inner ring having a second nonracewayed radially inner peripheral surface, said second radially outer ring having a second nonracewayed radially outer peripheral surface; and
 another ring structure which is situated substantially coplanarly intermediate said first rolling element bearing assembly and said second rolling element bearing assembly, said another ring structure having a circularly shaped radially outer peripheral structure surface and a circularly shaped radially inner peripheral structure surface, said circularly shaped radially inner peripheral structure surface being eccentric with respect to said circularly shaped radially outer peripheral structure surface, said circularly shaped radially outer peripheral structure surface being congruous with said first nonracewayed radially inner peripheral surface, said circularly shaped radially inner peripheral structure surface being congruous with said second nonracewayed radially outer peripheral surface, said ringlike structure thereby uniting said first rolling element bearing assembly and said second rolling element bearing assembly;

wherein said primary annulus includes said first radially inner ring and said secondary annulus includes said second radially inner ring.

9. An orbital device as in claim 8, wherein said ringlike structure includes a first ringlike substructure and a second ringlike substructure, said first ring substructure having said circularly shaped radially outer peripheral structure surface and an irregularly shaped radially inner peripheral substructure surface, said second ring substructure having said circularly shaped radially inner peripheral structure surface and an irregularly shaped radially outer peripheral substructure surface, said irregularly shaped radially inner peripheral substructure surface mating with said irregularly shaped radially outer peripheral substructure surface.

10. An orbital device as in claim 9, wherein said object has an object outer surface, and wherein said orbital device comprises an adaptor having an aperture and a circularly shaped radially outer peripheral adaptor surface, said aperture having a selectively shaped radially inner peripheral adaptor aperture surface, said circularly shaped radially outer peripheral adaptor surface being congruous with said second nonracewayed radially inner peripheral surface, said selectively shaped radially inner peripheral adaptor aperture surface accommodating said object outer surface.

11. Apparatus for imposing a rotatably variable bending force upon a non-rotating longitudinal structure, said apparatus comprising:

a diametrically major roller bearing assembly having a major outer ring, a plurality of major rolling elements, a major inner ring and a major imaginary axis;

a diametrically minor roller bearing assembly having a minor outer ring, a plurality of minor rolling elements, a minor inner ring and a minor imaginary axis;

means for rotating said major inner ring about said major axis;

means for coupling said major inner ring and said minor outer ring whereby said major roller bearing assembly and said minor roller bearing assembly are nonconcentric and approximately coplanar diametrically, and whereby said minor inner ring freely rotates about said minor axis and revolves about said major axis as said major inner ring is rotated about said major axis; and means for securing said structure bilaterally with respect to said minor roller bearing assembly whereby said structure intersects said minor inner ring, and whereby said structure bends variably about said minor axis as said major inner ring is rotated about said major axis.

12. Apparatus for imposing a rotatably variable bending force as in claim 11, wherein:

said major roller bearing assembly has a major inside circumference;

said minor roller bearing assembly has a minor outside circumference; and said means for coupling includes a system having a system outside circumference and a system inside circumference, said system outside circumference being compatible with said major inside circumference, said system inside circumference being compatible with said minor outside circumference.

13. Apparatus for imposing a rotatably variable bending force as in claim 12, wherein said system includes a major subsystem and a minor subsystem, said major subsystem having said system outside circumference and a noncircular major subsystem inside periphery, said minor subsystem having said system inside circumference and a noncircular minor subsystem outside periphery which is compatible with said noncircular major subsystem inside periphery.

14. Apparatus for imposing a rotatably variable bending force as in claim 11, wherein said structure has two longitudinal ends, and wherein said apparatus comprises means, proximate at least one said end, for applying an axial force.

15. Apparatus for imposing a rotatably variable bending force as in claim 11, wherein said structure has two longitudinal ends, and wherein said apparatus comprises means, between said minor roller bearing assembly and at least one said end, for applying a torsional force.

16. Apparatus for imposing a rotatably variable bending force as in claim 11, wherein said structure has two longitudinal ends, and wherein said apparatus comprises:

means, proximate at least one said end, for applying an axial force; and means, between said minor roller bearing assembly and at least one said end, for applying a torsional force.

17. Method for imposing a rotatably variable bending force upon a non-rotating longitudinal structure, said method comprising:

providing a diametrically major roller bearing assembly having a major outer ring, a plurality of major rolling elements, a major inner ring and a major imaginary axis;

providing a diametrically minor roller bearing assembly having a minor outer ring, a plurality of minor rolling elements, a minor inner ring and a minor imaginary axis;

coupling said major inner ring and said minor outer ring whereby said major roller bearing assembly and said minor roller bearing assembly are nonconcentric and approximately coplanar diametrically, and whereby said minor inner ring freely rotates about said minor axis and revolves about said major axis as said major inner ring is rotated about said major axis;

securing said structure bilaterally with respect to said minor roller bearing assembly whereby said structure intersects said minor inner ring, and whereby said structure bends variably about said minor axis as said major inner ring is rotated about said major axis; and rotating said major inner ring about said major axis.

18. Method for imposing a rotatably variable bending force as in claim 17, wherein:

said major roller bearing assembly has a major inside circumference;

said minor roller bearing assembly has a minor outside circumference; and said coupling includes joining a system with said major inner ring and said minor outer ring, said system having a system outside circumference and a system inside circumference, said system outside circumference being compatible with said major inside circumference, said system inside circumference being compatible with said minor outside circumference.

19. Method for imposing a rotatably variable bending force as in claim 18, wherein said system includes a major subsystem and a minor subsystem, said major subsystem having said system outside circumference and a noncircular major subsystem inside periphery, said minor subunit having said unit inside circumference and a noncircular minor subsystem outside periphery which is compatible with said noncircular major subsystem inside periphery.

20. Method for imposing a rotatably variable bending force as in claim 17, wherein said structure has two longitudinal ends, and wherein said method comprises applying at least one force selected from the group of forces consisting of an axial force and a torsional force, said axial force being applied at at least one said end, said torsional force being applied between said minor roller bearing assembly and at least one said end.

* * * * *